United States Patent
Arita et al.

(10) Patent No.: US 10,529,549 B2
(45) Date of Patent: Jan. 7, 2020

(54) METHOD FOR ANALYZING OPTICAL ISOMERS USING CIRCULARLY POLARIZED LIGHT AND ION MOBILITY ANALYZER

(71) Applicant: SHIMADZU CORPORATION, Kyoto-shi, Kyoto (JP)

(72) Inventors: Yoshinori Arita, Kyoto (JP); Osamu Furuhashi, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 16/108,182

(22) Filed: Aug. 22, 2018

(65) Prior Publication Data
US 2019/0066992 A1    Feb. 28, 2019

(30) Foreign Application Priority Data
Aug. 23, 2017 (JP) .................................. 2017-159863

(51) Int. Cl.
*H01J 49/06* (2006.01)
*G01N 27/62* (2006.01)
*G01N 21/19* (2006.01)

(52) U.S. Cl.
CPC .............. *H01J 49/06* (2013.01); *G01N 21/19* (2013.01); *G01N 27/622* (2013.01)

(58) Field of Classification Search
CPC ........ G01N 27/622; G01N 1/44; G01N 21/19; G01N 2021/216; H01J 49/004
See application file for complete search history.

(56) References Cited

U.S. PATENT DOCUMENTS 7,081,618 B2    7/2006  Laprade
8,884,221 B2 *  11/2014 Wu ...................... G01N 27/622
                                                250/288

(Continued)

FOREIGN PATENT DOCUMENTS

JP    2005-321233 A    11/2005

OTHER PUBLICATIONS

Toshiki Sugai, "Ion Mobility and Mass Spectrometry-Gas Phase Mobility", TMS Study Group, 17 pages.
(Continued)

*Primary Examiner* — Brooke Purinton
(74) *Attorney, Agent, or Firm* — Sughrue Mion, PLLC

(57) ABSTRACT

The existence ratio of optical isomers (D-form, L-form) is easily measured.
Counterclockwise or clockwise circularly polarized light is applied from a light application unit 6 to ions which are derived from a target compound and are drifting in a drift region 3. The ions absorb light, and a collision cross-section of the ions thus changes, whereby the mobility also changes. Each of the D-form and the L-form has a light absorption rate which is different between counterclockwise circularly polarized light and clockwise circularly polarized light. Therefore, each light absorption rate is examined in advance, and an existence ratio of the D-form and the L-form is calculated, based on the two intensity ratios each of which is the ratio of a peak of the ions having absorbed no light and a peak of the ions having absorbed light, which peaks appear on a drift time spectrum, and based on the light absorption rates of the D-form and the L-form.

6 Claims, 4 Drawing Sheets

(56) References Cited

U.S. PATENT DOCUMENTS

| | | | | |
|---|---|---|---|---|
| 2004/0178340 A1* | 9/2004 | Karas | ............... | G01N 27/622 |
| | | | | 250/282 |
| 2007/0016080 A1* | 1/2007 | Alfano | ............. | A61B 5/0066 |
| | | | | 600/476 |
| 2008/0173809 A1* | 7/2008 | Wu | ..................... | C07B 63/00 |
| | | | | 250/283 |
| 2013/0258334 A1* | 10/2013 | Sunami | ............... | G01J 3/447 |
| | | | | 356/327 |
| 2017/0003169 A1* | 1/2017 | Shaltout | ............ | G01J 3/447 |
| 2019/0137447 A1* | 5/2019 | Campbell | .......... | G01N 27/62 |

OTHER PUBLICATIONS

Prabha Dwivedi et al., "Gas Phase Chiral Separation by Ion Mobility Spectrometry", Analytical Chemistry, Dec. 15, 2006, 17 pages, vol. 78., No. 24.

* cited by examiner

METHOD FOR ANALYZING OPTICAL ISOMERS USING CIRCULARLY POLARIZED LIGHT AND ION MOBILITY ANALYZER

TECHNICAL FIELD

The present invention relates to a method for analyzing optical isomers of a predetermined compound contained in a sample and relates to an ion mobility analyzer for use in the analysis.

BACKGROUND ART

It is known that biological compounds such as amino acids and sugars often have optical isomers (also referred to as enantiomers). It is known that optical isomers are generally distinguished as the D-form and the L-form, and the properties and actions are different between the D-form and the L-form in vivo. As disclosed in Patent Literature 1, for example, an increase in an optical isomer of a specific compound may be used as a marker of a specific disease. In addition, some reports point out that an increase in an optical isomer of a specific compound may cause a specific disease. Therefore, in the fields of medicine, pharmaceutical development, food, and the like, there is a need for a method by which optical isomers (D-form, L-form) of a compound are easily distinguished and by which the ratio of the optical isomers (optical purity) is easily calculated.

Conventionally, liquid chromatography is used to separate optical isomers in a sample. In addition, in order to detect or distinguish the separated optical isomers, optical measurement such as circular dichroism (CD) measurement or optical rotation measurement based on a light absorption spectrum is used. However, generally, analysis by such methods takes time. In addition, in order to use such methods, an adequate amount of sample is necessary, and it is difficult to use the methods when the amount of sample is very small.

Apart from the above analytical methods, a method for analyzing optical isomers using ion mobility spectrometry (IMS) is conventionally known. When molecular ions generated from a compound contained in a sample are moved in a medium gas (or liquid) by the action of an electric field, the ions move at a speed corresponding to mobility that depends on a collision cross-section depending on the size or the like of the molecule and that depends on the strength of the electric field. The IMS method is a measurement method using this mobility for analysis of sample molecules (see Patent Literature 2, for example).

The structures of the D-form and the L-form, which are optical isomers, are in a mirror image relation and have the same mass and size, so that there is no difference in a collision cross-section. Therefore, optical isomers cannot be separated by the general IMS method. Non Patent Literatures 1 and 2 disclose the following special analytical method. In this method, a chiral gas having a structure similar to the structure of a compound to be detected is mixed into a gas flowing in a region where ions are drifted in the IMS method. Then, an interaction that depends on chiral symmetry occurs between the compound molecular ions to be detected and the chiral gas, and the effective collision cross-section of the compound molecule ions to be detected changes. By using this characteristic, optical isomers can be separated and detected in the IMS method.

However, in the above method, it is necessary to prepare a chiral gas corresponding to the compound to be detected. Therefore, the method works well only when the compound is to be detected is a specific one or ones. If various compounds are to be detected, however, it is necessary to prepare various types of chiral gases corresponding to each of these compounds, and the measurement cost is accordingly high. In addition, for some kinds of compounds, an appropriate chiral gas cannot be prepared, and in such a case, the above analysis method cannot be used.

CITATION LIST

Patent Literature

Patent Literature 1: JP 2005-321233 A
Patent Literature 2: U.S. Pat. No. 7,081,618

Non Patent Literature

Non Patent Literature 1: "Ion Mobility and Mass Spectrometry-Gas Phase Mobility", Toshiki Sugai, TMS Study Group, [online](Searched on Internet on Jul. 12, 2017)
Non Patent Literature 2: "Gas Phase Chiral Separations by Ion Mobility Spectrometry", Prabha Dwivedi and two others, Analytical Chemistry, Dec. 15, 2006, 78 (24), pp. 8200-8206

SUMMARY OF INVENTION

Technical Problem

The present invention has been made to solve the above problems, and an object of the present invention is to provide a method for analyzing optical isomers by which optical isomers of various substances can be easily distinguished and quantified, and is to provide an ion mobility analyzer used for the analysis.

Solution to Problem

A method for analyzing optical isomers according to the present invention made to solve the above problems is a method for analyzing optical isomers of a target compound contained in a sample by using an ion mobility analyzer in which pulsed ions are introduced into a drift region, made to drift, separated in a traveling direction of the ions according to ion mobility, and detected. The method includes:

a) a light application step for applying counterclockwise or clockwise circularly polarized light to the ions which are derived from the target compound and which are to be introduced into the drift region or are drifting in the drift region;

b) a measurement step for measuring a relation between a drift time of the ions and an ion intensity of the ions when the counterclockwise or clockwise circularly polarized light is applied to the ions; and c) an optical isomer analysis step for distinguishing optical isomers of the target compound or estimating an existence ratio of the optical isomers, based on measurement results obtained in the measurement step.

In addition, an ion mobility analyzer according to the present invention is an apparatus used to carry out the method for analyzing optical isomers according to the present invention; and in the ion mobility analyzer, pulsed ions are introduced into a drift region, made to drift, separated in a traveling direction of the ions according to ion mobility, and detected. The ion mobility analyzer includes:

a) a light application unit which applies counterclockwise or clockwise circularly polarized light to the ions which are derived from the target compound and which are to be introduced into the drift region or are drifting in the drift region;

b) a spectrum obtaining unit which obtains a spectrum showing a relation between a drift time of the ions and an ion intensity of the ions when the counterclockwise or clockwise circularly polarized light is applied to the ions; and c) an optical isomer analysis unit which distinguishes optical isomers of the target compound or estimates an existence ratio of the optical isomers, based on the spectrum obtained by the spectrum obtaining unit.

It is known that light absorption efficiencies (light absorption cross-sections) for counterclockwise circularly polarized light and clockwise circularly polarized light are different between the D-form and the L-form which are optical isomers of the same compound. The above circular dichroism measurement is a method utilizing this characteristic. On the other hand, when ions derived from a compound are irradiated with light and the ions absorb the light, electron excitation is caused, and a collision cross-section of the ions changes. When the collision cross-section changes, the ion mobility changes; thus, a peak position (drift time) shifts on a drift time spectrum showing the relation between the ion drift time and the ion intensity (the number of ions).

Normally, the light absorption efficiency a by ions is not 100% (0%<α<100%). Therefore, the collision cross-section of some of the ions irradiated with light changes, but the collision cross-section of the other ions does not change. As a result, on the drift time spectrum, peaks corresponding to one compound are separated into two. The ratio of the intensity of the separated two peaks depends on the light absorption efficiencies of the ions. As described above, the light absorption efficiency of the optical isomer is different between counterclockwise circularly polarized light and clockwise circularly polarized light. Assuming that the target compound in the sample is only D-form or L-form, when either counterclockwise circularly polarized light or clockwise circularly polarized light is applied to the ions, the intensity ratio of the two peaks on the drift time spectrum is different depending on whether the target compound is D-form or L-form. As a result, it is possible to distinguish between the D-form and the L-form.

In addition, when the D-form and the L-form of the target compound are present in mixture, the intensity ratio of the two peaks based on the target compound and observed on the drift time spectrum under the application of either counterclockwise circularly polarized light or clockwise circularly polarized light is different depending on the existence ratio of the D-form and the L-form. The light absorption rate of each of the D-form and the L-form indicates the degree of contribution to the intensity of the peak of the ions whose collision cross-section has changed, in other words, the degree of contribution to the intensity of the peak with the drift time shifted due to the application of light. Therefore, if the light absorption rates of the D-form and the L-form are known, it is also possible to estimate the existence ratio of the D-form and the L-form by calculation based on the intensity ratio of the two peaks on the drift time spectrum and the light absorption rates of the D-form and the L-form.

That is, in the method for analyzing optical isomers according to the present invention using the ion mobility analyzer according to the present invention, in the measurement step, the drift time spectrum is obtained in a state where the counterclockwise or clockwise circularly polarized light is applied to the ions which are derived from a target compound and which are to be introduced into the drift region or are drifting in the drift region. Instead, an ion mobility spectrum in which a drift time is converted into ion mobility may be obtained. Then, in the optical isomer analysis step, from the ratio of the intensities of the two peaks based on the same compound and observed on the drift time spectrum and from the previously obtained light absorption rates of the D-form and the L-form with respect to both forms of circularly polarized light, the optical isomers of the target compound are distinguished, or the existence ratio of the optical isomers of the target compound is calculated.

As described above, in the method for analyzing optical isomers and the ion mobility analyzer according to the present invention, it is possible to distinguish the optical isomers and to determine the existence ratio of the optical isomers from the drift time spectrum obtained when either counterclockwise circularly polarized light or clockwise circularly polarized light is applied to the ions; however, it is more preferable to use a plurality of drift time spectra (or ion mobility spectra) obtained when the counterclockwise circularly polarized light and the clockwise circular polarized light are each applied to the ions.

That is, in the method for analyzing optical isomers according to the present invention, the following steps are preferable.

In the light application step, the counterclockwise circularly polarized light and the clockwise circularly polarized light are respectively applied to the ions.

In the measurement step, when the circularly polarized lights of respective directions are applied to the ions in the light application step, the relation between the drift time and the ion intensity of the ions is measured with respect to each direction.

In the optical isomer analysis step, on the basis of the plurality of measurement results obtained in the measurement step, the optical isomers of target compound are distinguished, or the existence ratio of the optical isomers is estimated.

In addition, in the ion mobility analyzer according to the present invention, the following configuration is preferable.

The light application unit can respectively apply the counterclockwise circularly polarized light and the clockwise circularly polarized light to the ions.

The spectrum obtaining unit obtains a spectrum with respect to each direction of the circularly polarized light when the circularly polarized lights of respective directions are applied to the ions by the light application unit.

The optical isomer analysis unit distinguishes the optical isomers of the target compound or estimates the existence ratio of the optical isomers on the basis of the plurality of spectra obtained by the spectrum obtaining unit.

According to the method for analyzing optical isomers using such an ion mobility analyzer, for example, when the ions derived from the target compound drift in the drift region, even if the existence ratio of optical isomers (D-form, L-form) is not uniform, even if the circularly polarized light by the light application unit is not evenly applied to the ions, or even if the difference of the light absorption rate between the D-form and the L-form with respect to the circularly polarized light in any one direction is small, the existence ratio of the optical isomer can be obtained more accurately.

Note that one embodiment of the ion mobility analyzer according to the present invention can be configured to include a detector that detects ions which are separated according to ion mobility in the drift region. In this configuration, a drift time spectrum and an ion mobility spectrum can be generated, based on the detection signal obtained by the detector.

Another aspect of the ion mobility analyzer according to the present invention may be configured to be an ion mobility-mass analyzer including a mass analysis unit which detects the ions by further separating, according to a mass-to-charge ratio, the ions having been separated according to the ion mobility in the drift region. In this configuration, the drift time spectrum and the ion mobility spectrum may be generated, based on the result of detection without separating the ions according to the mass-to-charge ratio in the mass analysis unit, or based on the result of detection by separating the ions according to the mass-to-charge ratio in the mass analysis unit.

By using the ion mobility-mass analyzer, even when another compound whose ion mobility is substantially the same as the ion mobility of the target compound is present in the sample, it is possible to separate, in the mass analysis unit, the ions derived from the another compound and the ions derived from the target compound. By this operation, the influence of such a coexisting compound is rejected, and it is thus possible to obtain a drift time spectrum and an ion mobility spectrum with higher precision.

Advantageous Effects of Invention

According to the method for analyzing optical isomers and the ion mobility analyzer according to the present invention, optical isomers (D-form, L-form) of a target compound contained in a sample can be easily distinguished. Further, even if the target compound mixedly includes D-form and L-form, it is possible to simply obtain the existence ratio of the D-form and the L-form.

DESCRIPTION OF EMBODIMENTS

Figure 3:
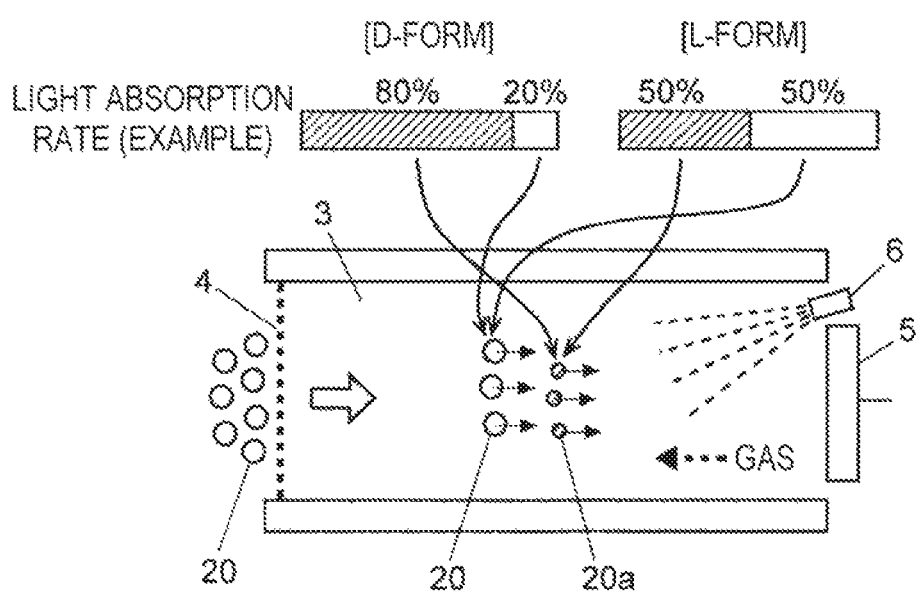
FIG. 3 is a schematic configuration diagram for illustrating a principle of a method for analyzing optical isomers using the ion mobility analyzer according to the present invention.
Figure 4:
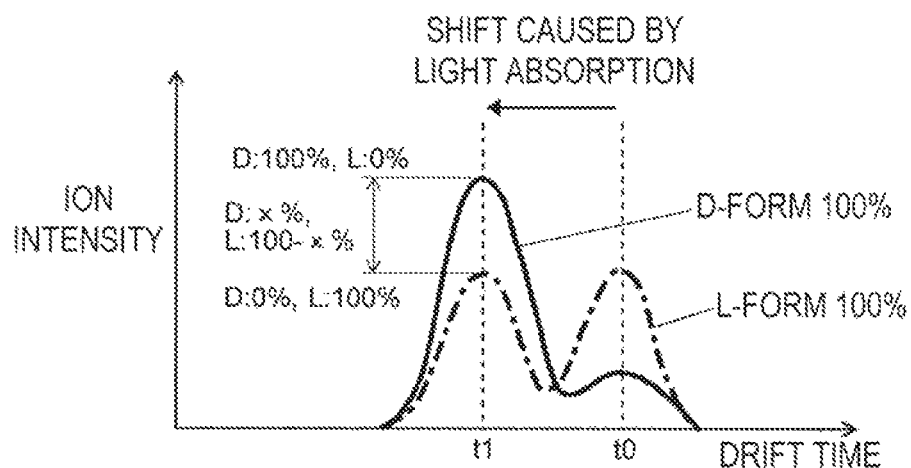
FIG. 4 is a diagram for illustrating the principle of the method for analyzing optical isomers using the ion mobility analyzer according to the present invention.

First, a principle of a method for analyzing optical isomers using an ion mobility analyzer according to the present invention will be described with reference to FIGS. 3 to 5. FIG. 3 is a diagram showing a principle configuration of the ion mobility analyzer according to the present invention, and FIG. 4 is a diagram for illustrating the principle of the method for analyzing optical isomers.

The ion mobility analyzer shown in FIG. 3 has a gate electrode 4 and a detector 5, respectively, on an inlet side and an outlet side of a drift tube 2 in which a drift region 3 is formed. This configuration is the same as the configuration of a general ion mobility analyzer. In addition, as a characteristic structural component, a light application unit 6 is provided which radiates predetermined light, specifically, counterclockwise or clockwise circularly polarized light toward the drift region 3.

Here, it is assumed that the target compound mixedly includes optical isomers (D-form, L-form). The ions 20 derived from the target compound are accumulated in front of the gate electrode 4, and are simultaneously introduced into the drift region 3 when the gate electrode 4 is opened for a short time. Then, the ions 20 drift in the drift region 3 and then reach the detector 5. Since the ions derived from the target compound have the same collision cross-section regardless of the optical isomers, the ion mobility is also the same. Therefore, when no light is radiated from the light application unit 6, all the ions derived from the target compound reach the detector 5 substantially simultaneously regardless of optical isomers. That is, it is impossible to distinguish optical isomers.

On the other hand, when circularly polarized light is applied to the ions which are drifting or just before drifting and when the ions absorb light, electron excitation occurs, and the collision cross-section of the ions changes. That is to say, when ions absorb light, ion mobility changes. However, since the optical absorption coefficient of the ions is not 100% and the optical isomers have circular dichroism, the D-form and the L-form have different light absorption rates with respect to counterclockwise circularly polarized light and clockwise circularly polarized light. When the ions are irradiated with counterclockwise or clockwise circularly polarized light from the light application unit 6 at the time of measurement, the ions 20a whose collision cross-section has changed (in this case, reduced) by absorbing the circularly polarized light have a larger ion mobility and reach the detector 5 sooner, than the ions 20 which do not absorb the circularly polarized light.

Figure 5:
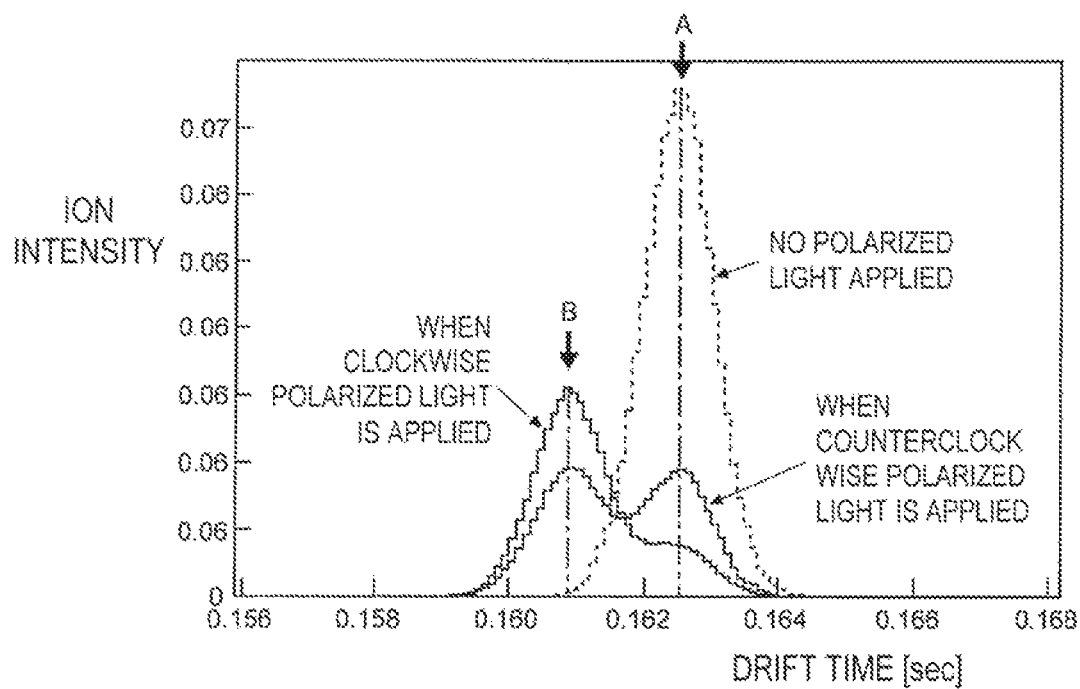
FIG. 5 is a conceptual diagram of a drift time spectrum obtained when ions are irradiated with each of clockwise circularly polarized light and counterclockwise circularly polarized light.

FIG. 5 shows a result of simulating how the drift time spectrum generated based on the detection signal obtained by the detector 5 changes when circularly polarized light is applied to the ions. In this simulation, the parameters and measurement conditions of the ion mobility analyzer were assumed as follows.

Drift length: 200 mm
Drift voltage (voltage difference between both ends of the drift region 3): 12 kV
Ambient temperature: 27° C.
Pressure: 1 atm
Open time of gate electrode: 0.1 msec
Resolution: R=130

Further, the characteristics of ions were assumed as follows.

Collision Cross-Section (CCS) of ions=2 $nm^2$ (ion mobility: K=1.97 $cm^2/Vs$) when no polarized light is applied
Change in collision cross-section of ions due to light absorption: from 2 $nm^2 \rightarrow 1.98$ $nm^2$
Ion light absorption rate—Clockwise polarized light: 80%, Counterclockwise polarized light: 50%

When no polarized light is applied, the peak appears at a position indicated by reference sign A in FIG. 5. On the other hand, when ions are irradiated with clockwise polarized light, the mobility of some ions changes, so that the peak is separated at two positions, a position represented by reference sign A and a position represented by reference sign B in FIG. 5. The intensity ratio of the two peaks is approximately 4:1, which corresponds to the light absorption rates. On the other hand, when ions are irradiated with counterclockwise polarized light, the peak is similarly separated into two, but since the light absorption rates are different, and the intensity ratio of the two peaks is approximately 1:1.

As described above, the light absorption rate for clockwise polarized light and counterclockwise polarized light is different between the D-form and the L-form. The light absorption rate depends on the type of compound and the wavelength of light, but here, for the sake of easy description, the light absorption rate is assumed as follows as an example.

D-formLight absorption rate for clockwise polarized light: 80%, Light absorption rate for counterclockwise polarized light: 50%

L-formLight absorption rate for counterclockwise polarized light: 80%, Light absorption rate for clockwise polarized light: 50%

In other words, the light absorption rate for the counterclockwise polarized light and the light absorption rate for the clockwise polarized light have completely opposite characteristics between the D-form and the L-form. Of course, there only has to be a difference between the light absorption rate for counterclockwise polarized light and the light absorption rate for clockwise polarized light, and the D-form and the L-form do not have to have completely opposite characteristics.

Assuming now that the light applied to the ions from the light application unit 6 is counterclockwise circularly polarized light and all the ions derived from the target compound to be measured are D-form (D-form is 100%), since the light absorption rate of the ions is 80%, a shape of the peak in the drift time spectrum should be as shown by the solid line in FIG. 4. At this time, the intensity ratio of the two peaks is approximately 4:1. On the other hand, assuming that the light applied to the ions from the light application unit 6 is clockwise circularly polarized light and all the ions derived from the target compound to be measured are L-form (L-form is 100%), since the light absorption rate of the ions is 50%, a shape of the peak in the drift time spectrum should be as shown by the dot-and-dash line in FIG. 4. At this time, the intensity ratio of the two peaks is approximately 1:1. When there is a difference in the light absorption rate between the counterclockwise circularly polarized light and the clockwise circularly polarized light and when the light absorption rate is known, it is possible to distinguish whether the target compound is D-form or L-form, on the basis of the shape of the drift time spectrum, more specifically, on the basis of the intensity ratio of the two peaks.

Next, consideration is given to a state where the light applied to the ions from the light application unit 6 is clockwise circularly polarized light and where the D-form and the L-form are mixed, at an unknown ratio, as the ions derived from the target compound to be measured. In this case, since both the D-form and the L-form absorb light, it can be considered that the ions 20a, which are traveling ahead of the other ions in FIG. 3, include the D-form whose light absorption rate is 80% and the L-form whose light absorption rate is 50%. On the contrary, it can be considered that the ions 20, which are traveling behind the other ions, include the D-form which did not absorb light at the percentage of 20% and the L-form which did not absorb light at the percentage of 50%. Therefore, the intensity of the peak at time t1 in the drift time spectrum should be between the peak indicated by the solid line and the peak indicated by the dot-and-dash line in FIG. 4.

At this time, the degree of contribution of the D-form to the peak intensity at time t1 is obtained by multiplying the proportion of the D-form by the light absorption rate (80%) of the D-form, and the degree of contribution of the L-form is obtained by multiplying the proportion of the L-form by the light absorption rate (50%) of the L-form. On the other hand, the degree of contribution of the D-form to the peak intensity at time t0 is obtained by multiplying the proportion of the D-form by the percentage (20%) at which the D-form did not absorb light, and the degree of contribution of the L-form is obtained by multiplying the proportion of the L-form by the percentage (50%) at which the L-form did not absorb light. Therefore, if the light absorption rate is known, it is possible to calculate the existence ratio of the D-form and the L-form from the intensity ratio of the two peaks.

That is, if the light absorption rate of each of the D-form and the L-forms is known, not only pure D-form or L-form can be distinguished, but also the existence ratio of the D-form and the L-form can be determined based on the intensity ratio of the two peaks separated on the drift time spectrum. Further, in the above description, the drift time spectrum obtained when the counterclockwise circularly polarized light is applied to the ions is used; however, it is also possible to similarly distinguish between the D-form and the L-form and to determine the existence ratio by using the drift time spectrum obtained when the clockwise circularly polarized light is applied to the ions.

As described above, the light absorption rate depends on the kind of the compound, the wavelength of the light, and the like. Therefore, it is preferable that the light absorption rates of the D-form and the L-form be previously measured, for each target compound to be measured, under the condition that the counterclockwise or clockwise circularly polarized light is being applied from the light application unit 6.

Figure 1:
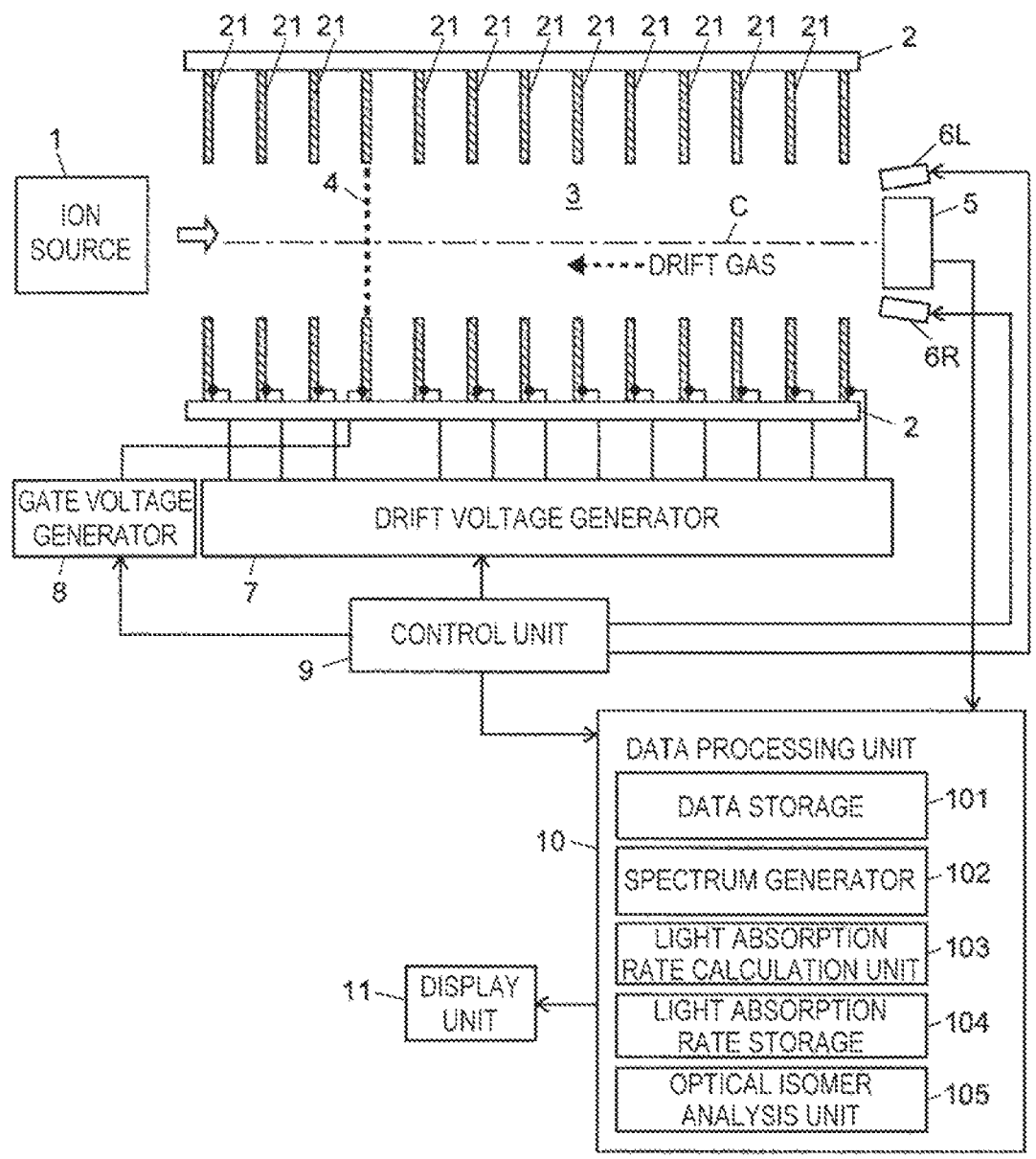
FIG. 1 is a schematic configuration diagram of an embodiment of an ion mobility analyzer according to the present invention.
Figure 2:
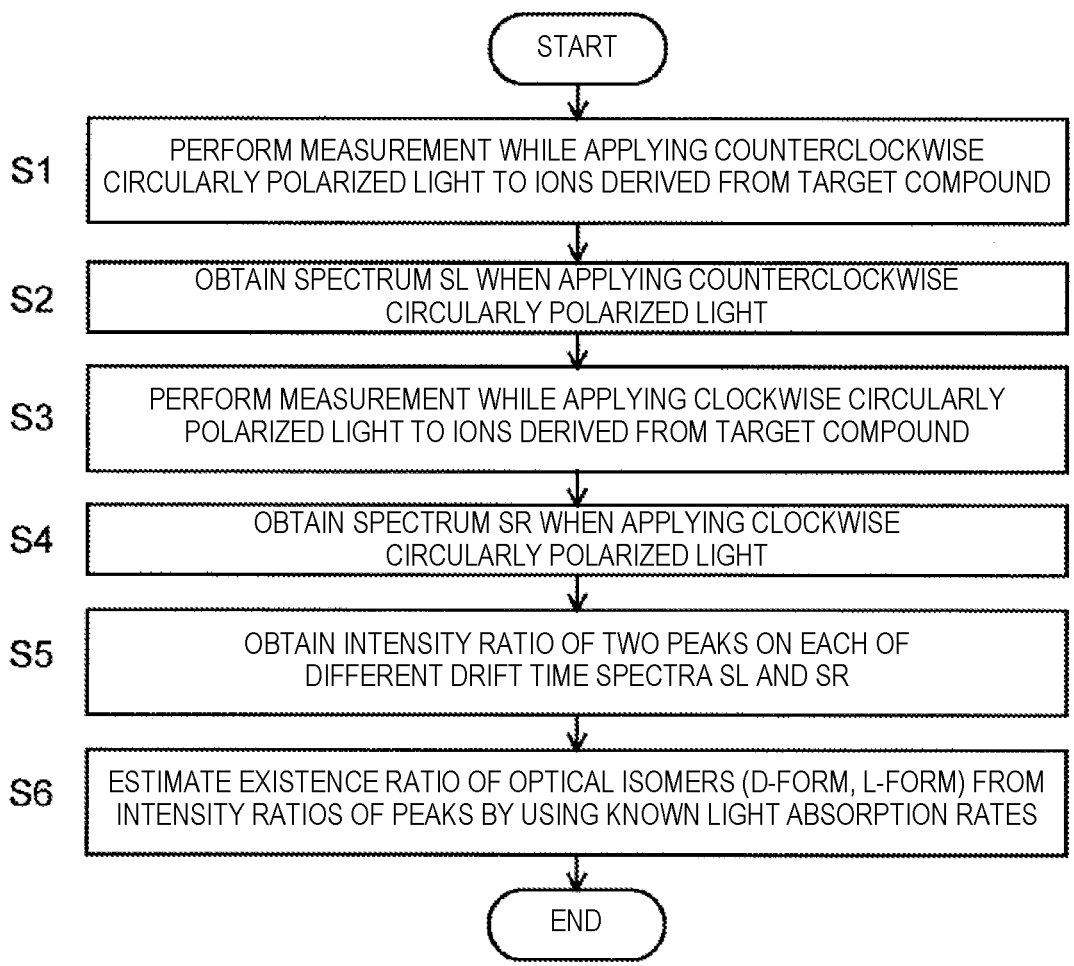
FIG. 2 is a flowchart showing a procedure of measurement and processing when an existence ratio of optical isomers is estimated in the ion mobility analyzer of the present embodiment.

Next, an embodiment of an ion mobility analyzer for analyzing optical isomers using the above principle will be described with reference to FIG. 1 and FIG. 2. FIG. 1 is a configuration diagram of a main part of the ion mobility analyzer of the present embodiment, and FIG. 2 is a flowchart illustrating a procedure of measurement and processing when the existence ratio of optical isomers is estimated in the ion mobility analyzer of the present embodiment.

The ion mobility analyzer of the present embodiment includes: an ion source 1 which ionizes a compound in a sample; a drift tube 2 inside which a plurality of annular electrodes 21 having the same shape are arranged along an ion optical axis (central axis) C, wherein a drift region 3 is formed inside the annular electrodes 21; a gate electrode 4 disposed on an inlet side of the drift tube 2; a detector 5 disposed on an outlet side of the drift tube 2; a first light application unit 6L and a second light application unit 6R which respectively radiate counterclockwise circularly polarized light and clockwise circularly polarized light in the drift region 3; a gate voltage generator 8 which applies a pulse voltage to the gate electrode 4 at a predetermined timing; and a drift voltage generator 7 which applies a predetermined voltage to each of the plurality of annular electrodes 21. The ion mobility analyzer further includes: a data processing unit 10 which processes data obtained by the detector 5; a display unit 11 which outputs a processing result; and a control unit 9 which controls the operation of each unit.

The data processing unit 10 includes, as functional blocks, a data storage 101, a spectrum generation unit 102, a light absorption rate calculation unit 103, a light absorption rate storage 104, and an optical isomer analysis unit 105. For example, the actual component of the data processing unit 10 is a personal computer, and the function of each of the above blocks can be realized by causing dedicated processing software installed in the computer to operate on the computer.

As described above, in order to distinguish optical isomers and to calculate an existence ratio, either counterclockwise circularly polarized light or clockwise circularly polarized light only has to be applied to the ions; however, in the apparatus of the present embodiment, in order to increase the accuracy of calculation of the existence ratio of the isomers, counterclockwise circularly polarized light and clockwise circularly polarized light are respectively applied to the ions.

First, an operation of the ion mobility analyzer of the present embodiment at the time of measuring ion mobility will be described.

When a predetermined DC voltage is applied to each annular electrode 21 from the drift voltage generator 7, an accelerating electric field is formed in the drift region 3 so as to accelerate the ions rightward in FIG. 1. Further, in the drift region 3, a flow of buffer gas is created at a constant flow velocity in the direction opposite to the traveling of the ions, and the gas keeps the gas pressure in the drift region 3 at substantially the atmospheric pressure. The ion source 1 ionizes a compound in a sample introduced from outside by a predetermined ionization method. This ionization method is not particularly limited, but when the sample is a liquid sample, for example, an electrospray ionization method or the like can be used.

The gate voltage generator 8 accumulates the ions in front of the gate electrode 4 by applying a voltage to block the ions, for example, applying a high positive voltage to the gate electrode 4 when the ions are positive ions. Then, a voltage for letting the ions pass through is applied to the gate electrode 4 for a short time at a predetermined timing. By this operation, the accumulated ions pass through the gate electrode 4 in a pulsed manner and are introduced into the drift region 3. The ions drift through the drift region 3 due to the action of the accelerating electric field against the flow of the buffer gas. At this time, the ions reach the detector 5, being spatially separated according to their mobility. The behavior of such ions is basically the same as the behavior in the principle configuration shown in FIG. 3.

Next, an operation of examining the existence ratio of the optical isomers in the ion mobility analyzer of the present embodiment will be described.

As described above, it is necessary to obtain the light absorption rate of each of the D-form and the L-form of the target compound for counterclockwise circularly polarized light and clockwise circularly polarized light, as an advance preparation. Therefore, samples of pure D-form and L-form of a target compound are prepared, each sample is measured with the present device, and the light absorption rates are calculated from the thus obtained drift time spectra. That is, for example, a sample containing pure D-form is used as a sample to be measured, and ion mobility measurement is performed by irradiating ions with counterclockwise circularly polarized light from the first light application unit 6L. In the data processing unit 10, the spectrum generation unit 102 generates a drift time spectrum, based on the obtained data. As long as the light absorption rate is not 100% or 0%, two peaks as indicated by solid lines in FIG. 4 are observed in the drift time spectrum. In this case, the peaks whose drift time is shifted are totally caused by light absorption by the D-form. Then, the light absorption rate calculation unit 103 calculates the light absorption rate from the intensity ratio of the two peaks.

By changing the direction of the circularly polarized light applied to the ion and by changing the sample to be measured to a substance containing a pure L-form, the light absorption rates of the D-form and the L-form of the target compound are obtained with respect to each of the counterclockwise circularly polarized light and the clockwise circularly polarized light and are stored in the light absorption rate storage 104. Note that, instead of a user experimentally obtaining light absorption rates, a manufacturer of the device may previously obtain light absorption rates experimentally for various compounds and may provide the light absorption rates to users as part of data processing software. In that case, it is not necessary for a user to measure a light absorption rate as described above.

In order to examine the existence ratio of the D-form and the L-form of a target compound in a sample, the sample is introduced into the ion source 1 under the control of the control unit 9, and the mobility of the ions derived from the target compound in the sample is measured while counterclockwise circularly polarized light is being applied to the ions from the first light application unit 6L (step S1). The data obtained by the detector 5 at this time is once stored in the data storage 101. Based on the collected data, the spectrum generation unit 102 generates a drift time spectrum SL at the time of applying the counterclockwise circularly polarized light (step S2). Next, the same sample is introduced into the ion source 1 under the control of the control unit 9, and the mobility of the ions derived from the target compound in the sample is measured while clockwise circularly polarized light is being applied to the ions from the second light application unit 6R (step S3). Based on the collected data, the spectrum generation unit 102 generates a drift time spectrum SR at the time of applying the clockwise circularly polarized light (step S4).

The optical isomer analysis unit 105 detects, with respect to each of the two drift time spectra SL and SR, the peak based on the ions having absorbed light and the peaks based on the ions having absorbed no light, and the intensity ratios of the two peaks are obtained (Step S5). Then, calculation is performed using the intensity ratio of the peaks and the information on the light absorption rates stored in the light absorption rate storage 104, and the existence ratio of the D-form and the L-form is thus calculated (step S6). As described above, since the existence ratio can be obtained from one drift time spectrum, it is possible to obtain a more accurate result by averaging the existence ratios each obtained from each of the two drift time spectra. The thus obtained result may be output on the display unit 11.

Of course, in the case that the target compound contained in the sample is only the D-form or the L-form, in order to see which one of the two is contained, it can be immediately determined from the intensity ratio of the two peaks and the light absorption rate. Further, if there is a large difference between each of the existence ratios of the optical isomers obtained from each of two drift time spectra, there may be a problem that, for example, ions are contained which have approximately the same ion mobility and are derived from another compound. Therefore, for example, if the difference between each of the existence ratios of the optical isomers obtained from each of two drift time spectra is equal to or larger than a predetermined threshold value, a warning display indicating that the measurement is suspicious may be performed.

In the ion mobility analyzer of the above embodiment, circularly polarized light is applied to the drifting ions, but electrons excited by light absorption do not immediately return to the original state (ground state). When circularly polarized light is applied to the ions immediately before the ions start to substantially drift, a collision cross-section is changed due to light absorption, generating a difference in mobility from the ions having absorbed no light. Therefore, circularly polarized light may be applied to the ions before drifting.

Further, since the above embodiment is merely an example of the present invention, the present invention is not limited to the above embodiment or the above various modifications, and it is obvious that changes, modifications, and additions appropriately made within the scope of the spirit of the present invention are included in the scope of the claims of the present application.

For example, in the ion mobility analyzer of the above embodiment, the ions separated according to the ion mobility in the drift region 3 are detected as they are; however, being separated in the drift region 3, the ions may be introduced into a mass separator such as a quadrupole mass filter so as to be further separated according to a mass-to-charge ratio. That is, the ion mobility analyzer may be configured to be an ion mobility-mass analyzer. In such a configuration, for example, even if the ions derived from a target compound and the ions derived from a different type of compound (impurity) have almost the same mobility and cannot be separated in the drift region 3, separation can be possible in the subsequent mass separation unit in some cases. Then, by generating the drift time spectrum based on the ion intensity information after the ions are separated in the mass separation unit, the existence ratio of the optical isomers of the target compound is calculated with the influence of the impurities removed.

REFERENCE SIGNS LIST

1 . . . Ion Source
2 . . . Drift Tube
21 . . . Annular Electrode
3 . . . Drift Region
4 . . . Gate Electrode
5 . . . Detector
6, 6L, 6R . . . Light Application Unit
7 . . . Drift Voltage Generator
8 . . . Gate Voltage Generator
9 . . . Control Unit
10 . . . Data Processing Unit
101 . . . Data Storage
102 . . . Spectrum Generation Unit
103 . . . Light Absorption Rate Calculation Unit
104 . . . Light Absorption Rate Storage
105 . . . Optical Isomer Analysis Unit
11 . . . Display Unit

The invention claimed is:

1. A method for analyzing optical isomers of a target compound contained in a sample by using an ion mobility analyzer in which ions are introduced into a drift region, made to drift, separated in a traveling direction of the ions according to ion mobility, and detected, the method comprising:
   a) a light application step of applying counterclockwise or clockwise circularly polarized light to the ions which are derived from the target compound and which are to be introduced into the drift region or are drifting in the drift region;
   b) a measurement step of measuring a relation between a drift time of the ions and an ion intensity of the ions when the counterclockwise or clockwise circularly polarized light is applied to the ions; and
   c) an optical isomer analysis step of distinguishing optical isomers of the target compound or estimating an existence ratio of the optical isomers, based on measurement results obtained in the measurement step.

2. The method for analyzing optical isomers according to claim 1, wherein
   in the light application step, the counterclockwise circularly polarized light and the clockwise circularly polarized light are respectively applied to the ions,
   in the measurement step, when the circularly polarized lights of respective directions are applied to the ions in the light application step, the relation between the drift time and the ion intensity of the ions is measured with respect to each direction, and
   in the optical isomer analysis step, based on the plurality of measurement results obtained in the measurement step, the optical isomers of the target compound are distinguished, or the existence ratio of the optical isomers is estimated.

3. An ion mobility analyzer in which ions are introduced into a drift region, made to drift, separated in a traveling direction of the ions according to ion mobility, and detected, the ion mobility analyzer comprising:
   a) a light application unit which applies counterclockwise or clockwise circularly polarized light to the ions which are derived from the target compound and which are to be introduced into the drift region or are drifting in the drift region; and
   b) a processor configured to
      obtain a spectrum showing a relation between a drift time of the ions and an ion intensity of the ions when the counterclockwise or clockwise circularly polarized light is applied to the ions; and
      distinguish optical isomers of the target compound or estimate an existence ratio of the optical isomers, based on the obtained spectrum.

4. The ion mobility analyzer according to claim 3, wherein
   the light application unit includes a first light source configured to apply the counterclockwise circularly polarized light to the ions and a second light source configured to apply the clockwise circularly polarized light to the ions;
   the processor obtains, when the circularly polarized lights of respective directions are applied to the ions by the light application unit, a spectrum with respect to each direction; and
   the processor distinguishes the optical isomers of the target compound or estimates the existence ratio of the optical isomers, based on the obtained plurality of spectra.

5. The ion mobility analyzer according to claim 3, wherein the ion mobility analyzer is an ion mobility-mass analyzer which includes a mass analysis unit which detects the ions by further separating, according to a mass-to-charge ratio, the ions which are separated according to the ion mobility in the drift region.

6. The ion mobility analyzer according to claim 4, wherein the ion mobility analyzer is an ion mobility-mass analyzer which includes a mass analysis unit which detects the ions by further separating, according to a mass-to-charge ratio, the ions which are separated according to the ion mobility in the drift region.

* * * * *